United States Patent
Mast et al.

(10) Patent No.: US 9,161,800 B2
(45) Date of Patent: Oct. 20, 2015

(54) ROBOTIC ARMS

(71) Applicant: SYNTHES USA, LLC, West Chester, PA (US)

(72) Inventors: Jeffrey W Mast, Reno, NV (US); Ralph F Polimeni, Jr., Reno, NV (US); John S Sargent, Reno, NV (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 138 days.

(21) Appl. No.: 13/848,141

(22) Filed: Mar. 21, 2013

(65) Prior Publication Data

US 2013/0218216 A1    Aug. 22, 2013

Related U.S. Application Data

(63) Continuation of application No. 12/788,689, filed on May 27, 2010, now Pat. No. 8,425,519.

(60) Provisional application No. 61/181,505, filed on May 27, 2009.

(51) Int. Cl.
*A61B 17/88* (2006.01)
*A61B 19/00* (2006.01)
(Continued)

(52) U.S. Cl.
CPC ........... *A61B 17/885* (2013.01); *A61B 17/6408* (2013.01); *A61B 17/66* (2013.01);
(Continued)

(58) Field of Classification Search
CPC .............. A61B 17/6408; A61B 17/66; A61B 17/8866; A61B 17/885; A61B 19/2203; A61B 2019/2223; A61B 2019/2226; A61B 2019/2234; A61B 2017/00539

USPC ........................... 606/54–59, 86 B, 86 R, 130
See application file for complete search history.

(56) References Cited

U.S. PATENT DOCUMENTS 6,001,108 A  *  12/1999  Wang et al. .................... 606/130
6,331,181 B1    12/2001  Tierney et al.
(Continued)

FOREIGN PATENT DOCUMENTS

EP      0386912      9/1990
JP    2002/017740    1/2002
(Continued)

OTHER PUBLICATIONS

Westphal; "Sensor-Based Surgical Robotics: Contributions to Robot Assisted Fracture Reduction"; XP009137259; Braunschweig; Aug. 29, 2007; pp. 11-81.

*Primary Examiner* — Pedro Philogene
(74) *Attorney, Agent, or Firm* — Fay Kaplun & Marcin, LLP

(57) ABSTRACT

A device for treating fractures of a bone comprises a plurality of arms, each extending from a proximal end to a distal end and movable in a three-dimensional space, the proximal end of each arm coupled to a frame and a plurality of couplings, each of the couplings coupled to a distal end of each of the plurality of arms, the coupling lockingly receiving a bone fixation element secured to a corresponding bone fragment such that each of the arms is coupled to a corresponding fragment of the bone in combination with a mechanical unit moving each of the arms relative to the frame and a controller receiving data corresponding to a desired final position of the fragments relative to one another and controlling the mechanical unit to move the arms relative to one another to achieve the desired final position of the bone fragments relative to one another.

15 Claims, 9 Drawing Sheets

(51) Int. Cl.
*A61B 17/64* (2006.01)
*A61B 17/66* (2006.01)
*A61B 17/00* (2006.01)

(52) U.S. Cl.
CPC ......... *A61B17/8866* (2013.01); *A61B 19/2203* (2013.01); *A61B 2017/00539* (2013.01); *A61B 2019/2223* (2013.01); *A61B 2019/2226* (2013.01); *A61B 2019/2234* (2013.01)

(56) References Cited

U.S. PATENT DOCUMENTS

| | | | |
|---|---|---|---|
| 7,507,240 B2* | 3/2009 | Olsen | 606/59 |
| 7,837,621 B2* | 11/2010 | Krause et al. | 600/300 |
| 7,875,039 B2 | 1/2011 | Vohra et al. | |
| 7,881,771 B2* | 2/2011 | Koo et al. | 600/426 |
| 8,167,880 B2* | 5/2012 | Vasta | 606/54 |
| 8,180,429 B2 | 5/2012 | Sasso | |
| 8,182,491 B2* | 5/2012 | Selover et al. | 606/104 |
| 2007/0225704 A1* | 9/2007 | Ziran et al. | 606/57 |
| 2008/0269741 A1 | 10/2008 | Karidis | |

FOREIGN PATENT DOCUMENTS

| | | |
|---|---|---|
| WO | 98/04203 | 2/1998 |
| WO | WO 2007/095662 | 8/2007 |
| WO | 2009/018398 | 2/2009 |

\* cited by examiner

ROBOTIC ARMS

PRIORITY CLAIM

The present application claims priority to U.S. Provisional Application Ser. No. 61/181,505 filed on May 27, 2009 entitled "Robotic Arms," the entire disclosure of which is incorporated herein by reference.

FIELD OF THE INVENTION

The present invention relates to devices for treating fractures and, in particular, relates to a device for reducing and/or holding fractured portions of the bone.

BACKGROUND

Fractures of bones may be difficult to treat due to displacement of fractured portions of the bone. Bone have attachments to muscles, tendons and ligaments, which tend to displace and angulate the bone, causing the fractured portions to move out of place. Thus, fractured portions must be realigned to achieve reduction. Realignment may require traction and correction of displacements and angulations via an application of force. For example, a surgeon or other medical professional may physically pull a patients foot or leg to distract the bone. Once proper reduction is obtained, the fractured portions of the bone must be held in position until fixation is applied to prevent re-displacement. However, the necessary force and the direction of the application required to correct displacements of the bone may be difficult to attain and maintain. Current methods do not allow the force, direction and the speed of the process to be gauged or controlled.

SUMMARY OF THE INVENTION

The present invention, directed to a device for treating fractures of a bone, comprises a plurality of arms, each extending from a proximal end to a distal end and movable in a three-dimensional space, the proximal end of each arm being coupled to a frame and a plurality of couplings, each of the couplings being coupled to a distal end of each of the plurality of arms, the coupling lockingly receiving a bone fixation element secured to a corresponding bone fragment such that each of the arms is coupled to a corresponding fragment of the bone in combination with a mechanical unit supplying motion to each of the arms relative to the frame and a controller receiving data corresponding to a position of the bone fragments relative to one another and controlling the motion to move the arms relative to one another to achieve the desired final position of the bone fragments relative to one another.

DETAILED DESCRIPTION

Figure 1:
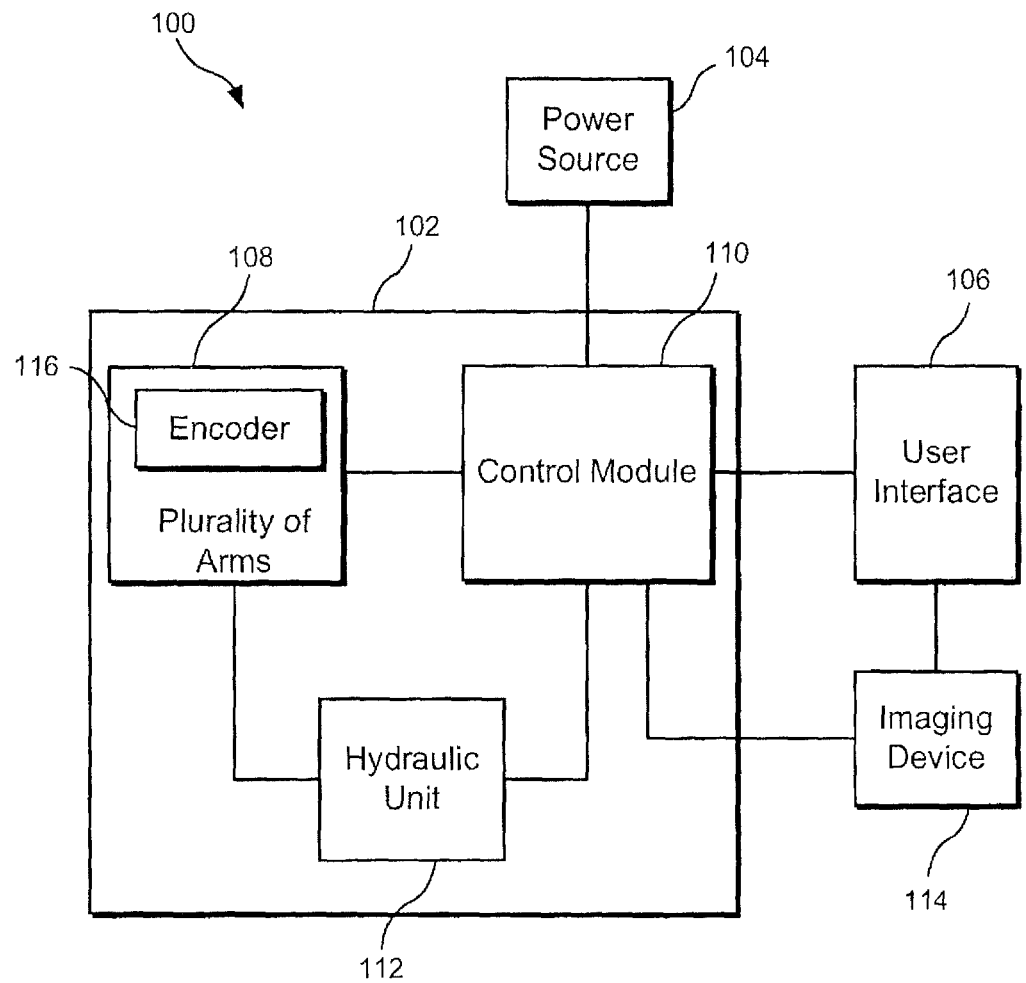
FIG. 1 shows a schematic view of a system according to an exemplary embodiment of the present invention.

The present invention may be further understood with reference to the following description and the appended drawings, wherein like elements are referred to with the same reference numerals. The present invention relates to devices for treating fractures and, in particular, relates to a device for reducing and/or holding fractured portions of the bone. Exemplary embodiments of the present invention provide a device including robotic arms that may be connected to the fractured bone to move the bone through all necessary axes to reposition fractured portions of the bone for fixation.

As shown in FIGS. 1-13, a system 100 according to an exemplary embodiment of the invention comprises a robotic device 102 for moving fractured portions of a bone 120 into a desired spatial relationship to one another. As shown in FIG. 1, the robotic device 102 is connectable to a power source 104 controlled via a user interface 106. The robotic device 102 may further comprise a control module 110 processing input from the user interface 106 to control movement of a plurality of alms 108 via, for example, hydraulic forces provided by a fluid pressurizing/compressing unit such as the hydraulic unit 112. Alternatively, the arms 108 may be moved by one or more servo motors (not shown) coupled thereto via any known gearing mechanism as would be understood by those skilled in the art. Each of the arms 108 may be connected to a target portion of the fractured bone 120 such that movement of the arms 108 repositions the fractured portions as desired. Each of the arms 108 may be equipped with an encoder 116 capable of precisely determining the position of the arm 108 such that the positions of the fractured portions of bone 120 may be accurately monitored and repositioned as desired.

The power source 104 may be any power source available in an operating room. For example, the power source 104 may be any source of electrical power, including a battery power. The power source 104 may be used to power the hydraulic unit 112 to move hydraulic fluid through the robotic device 102. As would be understood by those skilled in the art, the hydraulic fluid may be any suitably incompressible fluid such as, for example, mineral oil or saline. In another embodiment, the system 100 may use a compressible fluid for a fluid or pneumatic system 100. Instructions for the movement of the arms 108 may be inputted via the user interface 106 and processed by the control module 110 to control the hydraulic unit 112 in the manner necessary to achieve the desired motion indicated by the user as would be understood by those skilled in the art. The user interface 106 may be a simple switch and/or joystick arrangement for activating the robotic device 102 and directing movement of the arms 108. In a preferred embodiment, however, the user interface 106 may be a personal computer or other processing arrangement that may be used to input a direction of motion for each of the arms 108 and may also allow a user to specify a speed of movement of one or more of the arms. For example, the user may be able to assign vertex points to portions of the bone 120 and additional target points to which it is desired that the portions of the bone 120 be moved.

According to a further embodiment, the system 100 may also include an imaging device 114 for visualizing various fragments of the bone 120 such that the fractured portions are indicated on a screen of the imaging device. The system 100 may be capable of determining a position of each of the bone fragments relative to one another such that a user may input a final desired spatial relationship via the user interface 406. The position of each of the bone fragments 120 may be determined by the encoders 116 of the arms 108, which are connected to the bone fragments via the connectors 122.

Figure 2:
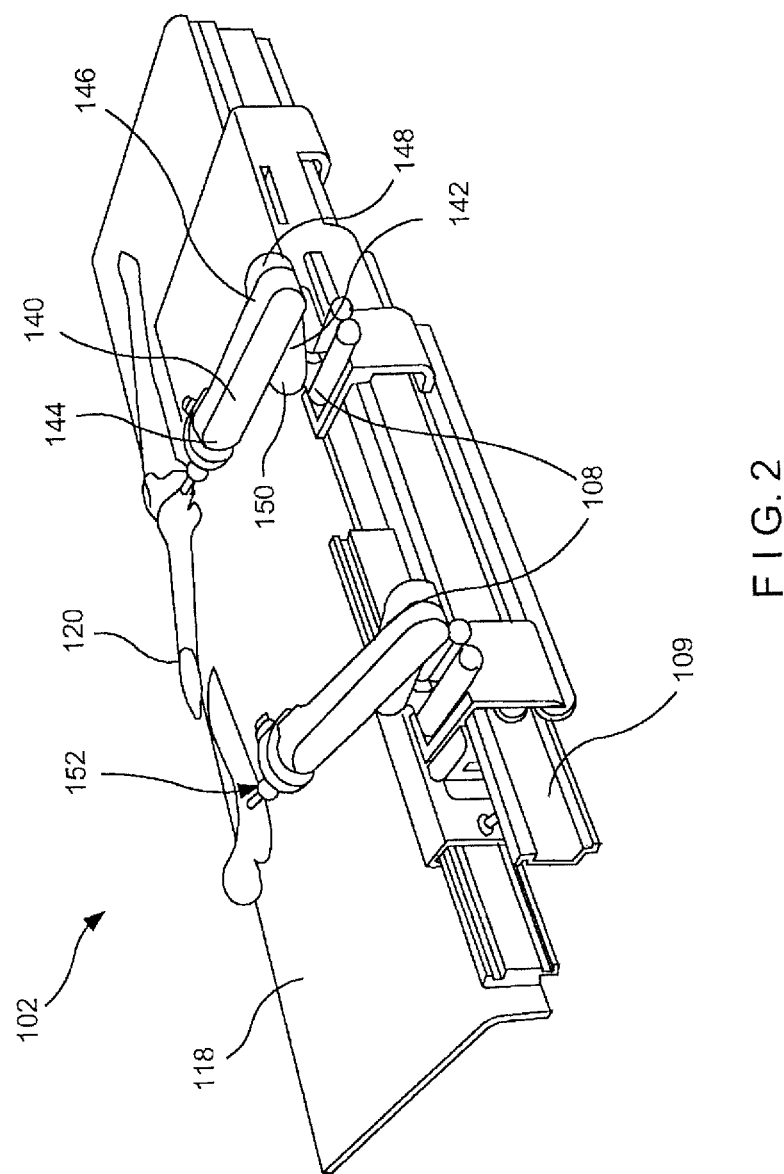
FIG. 2 shows a perspective view of a robotic device of the system of FIG. 1.

As shown in FIG. 2, the robotic device 102 may be mountable to an operating table 118 such that the arms 108 may be coupled to connectors 122 inserted into fractured portions of a bone 120. Alternatively, the robotic device 102 may be mounted on a separate table movable to a position alongside the operating table 118. The arms 108 may be mounted to a side of the table 118 via a longitudinal element 109 such that each of the arms 108 is slidable along the longitudinal element 109 to move longitudinally along the table 118. The longitudinal element 109 may also be movable relative to the table 118 via, for example, rotation. Although the figures show the robotic device 102 as including two arms 108, it will be understood by those of skill in the art that the robotic device 102 may include any number of arms 108.

The arms 108 are adapted to be movable through a three-dimensional space in six directions and six angulations to permit any desired positioning of the arms 108 relative to one another. To move in six directions, each of the arms 108 includes a first portion 140 and a second portion 142 rotatably coupled to one another. The first portion 140 extends from a first end 144 to a second end 146 and the second portion 142 extends from a first end 148 to a second end 150. The second end 146 of the first portion 140 is rotatably coupled to the first end 148 of the second portion 146 via, for example, a pin (not shown), such that the first portion 140 and the second portion 142 are rotatable relative to one another about the pin. It will be understood by those of skill in the art that the rotatable coupling of the first portion 140 and the second portion 142 of the arm 108 may function similarly to a human elbow. Additionally, the second end 150 of the second portion 144 of each of the arms 108 may be slidably coupled to the longitudinal element 109 such that the second portion 144 is also rotatable relative to the longitudinal element 109, permitting movement of the arms 108 relative to the table 118. Thus, it will be understood by those of skill in the art that the arms 108, along with the longitudinal element 109, permit movement of the arms 108 in a three-dimensional space to correct six displacements (e.g., anterior-posterior, medial-lateral and shortening-lengthening).

Figure 3:
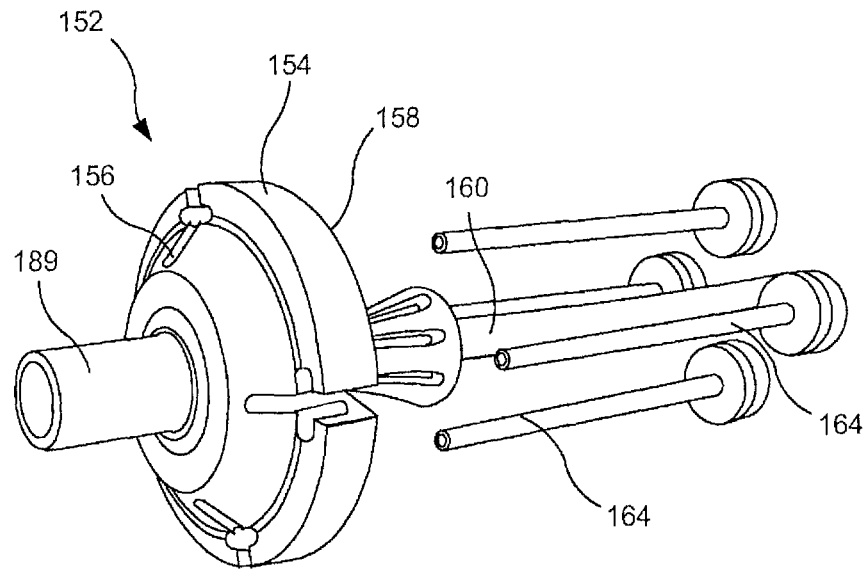
FIG. 3 shows a perspective view of a wrist portion of the robotic device of FIG. 1, in a first configuration.
Figure 4:
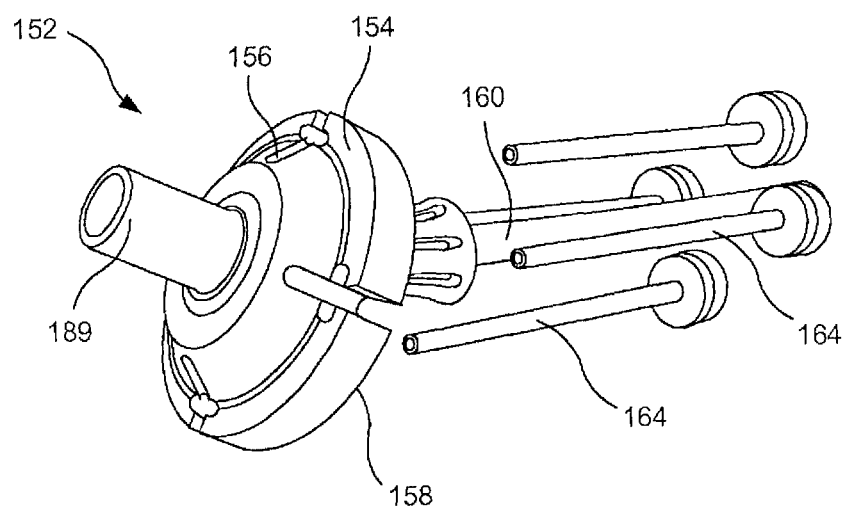
FIG. 4 shows a perspective view of the wrist portion of FIG. 3, in a second configuration.
Figure 5:
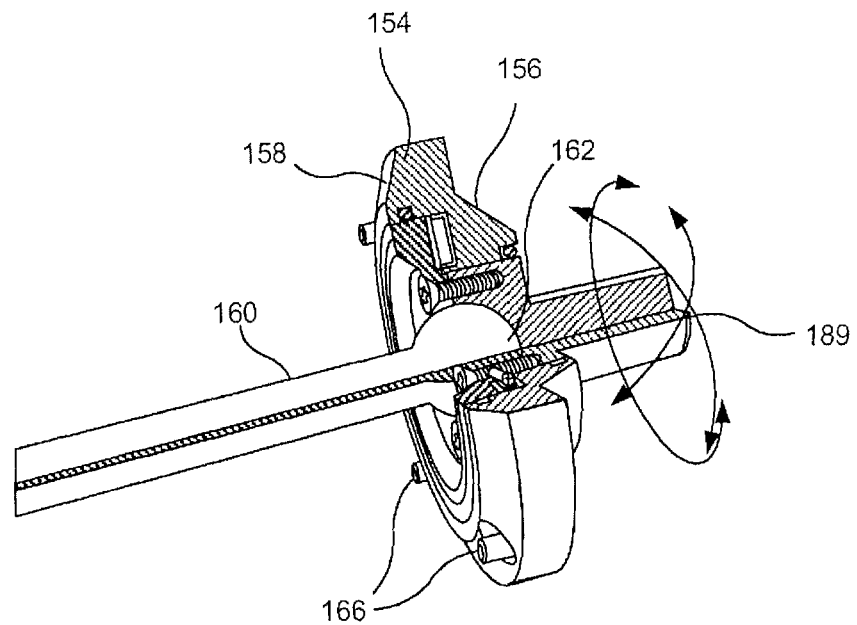
FIG. 5 shows an enlarged perspective view of a distal end of the wrist portion of FIG. 3.

The first portion 140 of the arm 108 may further include a wrist portion 152, which will be understood by those of skill in the art as functioning similarly to a human wrist. As shown in FIGS. 3-4, the wrist portion 152 includes a plate 154 supporting and positioning a spindle 189, which may be engaged to an end effector 136 (shown in FIGS. 9-13) for coupling to the connector 122. The end effector 136 may be, for example, a collet, chuck or jaws adapted to securely grasp the connectors 122. The plate 154 is also attached to a plurality of cylinders 164 that control movement of the plate 154 and the end effector 136 to provide a desired angulation of the end effector 136. The plate 154 may be attached to the cylinders 164 via, for example, a grouping of fibers, a cable or a shaft with a joint assembly. The plate 154 includes a distal surface 156 and a proximal surface 158, the spindle 189 being coupled to the distal surface 156 while the cylinders 164 are attached to the proximal surface 158. A shaft 160 providing axial support for the spindle 189 is coupled to the plate 154. As shown in FIG. 5, the shaft 160 may be coupled to the plate 154 via a pivot 162 received through the proximal surface 158 in a corresponding space 164 of the plate 154. The pivotable coupling allows the plate 154 to be angled and rotated about the pivot 162, permitting angulatory movement of the spindle 189 and thereby the end effector 136. In a preferred embodiment, the pivot 162 will be spherical such that the plate 154 may be angled in any desired direction. The cylinders 164 provide hydraulic forces for angling the plate 154 about the pivot 162, permitting angulations of the end effectors 136 to correct angular deformity in three planes (e.g., medial-lateral angulation, anterior-posterior angulation, internal and external radial angulation).

Figure 6:
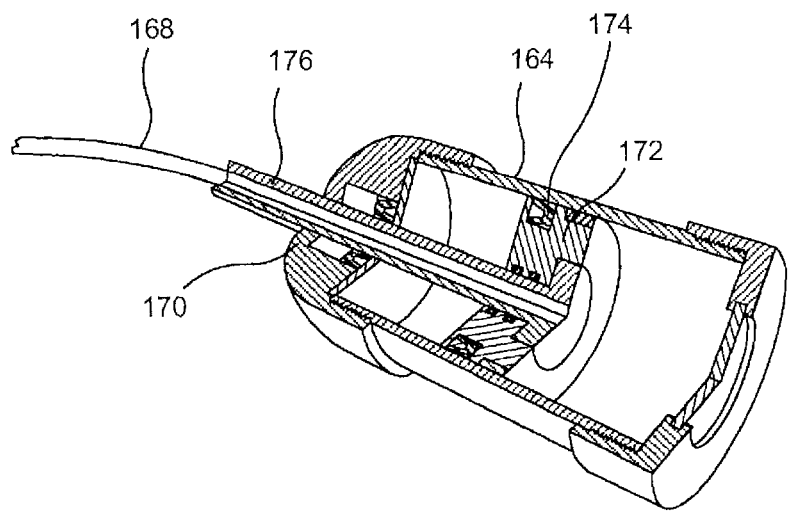
FIG. 6 shows a cylinder assembly of the wrist portion of FIG. 3.

The plate 154 may also include tendon attachment regions 166 for attaching to a fiber tendon 168 of each of the cylinders 164. The tendon attachment regions 166 may be positioned on the proximal surface 156 about a perimeter of the plate 154. Fluid movement through each of the cylinders 164 provided by the hydraulic unit 112 translates into a force on each of the tendons 168 attached to the plate 154 such that the force on the tendons 168 moves the plate 154 about the pivot 160, and therefore the attached spindle 189, in various angulations. In a preferred embodiment, the wrist portion 152 may include four cylinders 164 and four corresponding tendon attachment regions 166. However, it will be understood by those of skill in the art that any number of cylinders 164 may be included so long as the number of cylinders 164 is sufficient to provide complete angulation of the plate 154 and the spindle 189 through the desired range of movement. As shown in FIG. 6, the tendon 168 may extend from within the cylinder 164 past a distal end 170 of the cylinder 164. The cylinder may include a piston 172 fluid-sealed via a seal 174. The piston 170 may be connected to a rod 176 through which the tendon 166 extends. Thus, hydraulic force supplied by the hydraulic unit 112 through the cylinder 164 is provided to the tendon 168 extending therefrom to translate into movement of the plate 154. Although the cylinders 164 are described as being attached to the plate 154 via fiber tendons 168, it will be understood by those of skill in the art that the cylinders 164 may be attached to the plate 154 via a variety of attaching elements such as, for example, a cable or a shaft with a joint assembly.

In an alternative embodiment, movement of the plate 154 may be provided by a linear movement mechanism comprising gears, belts or a lead screw arrangement. The linear movement mechanism may also be attached to the plate 154 via, for example, fibers, a cable or a shaft with a joint assembly.

Figure 7:
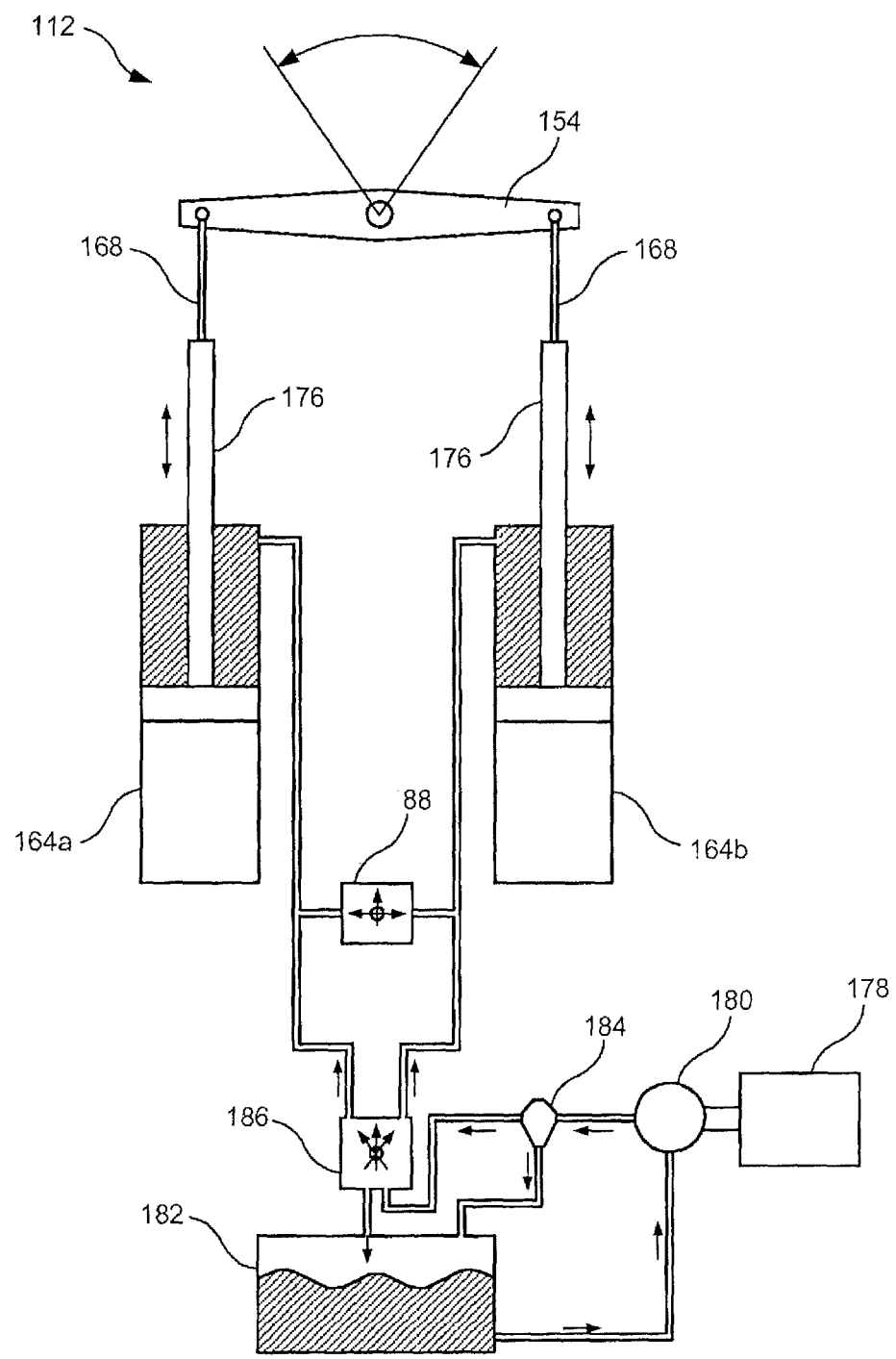
FIG. 7 shows a schematic diagram of a hydraulic unit of the system of FIG. 1.
Figure 8:
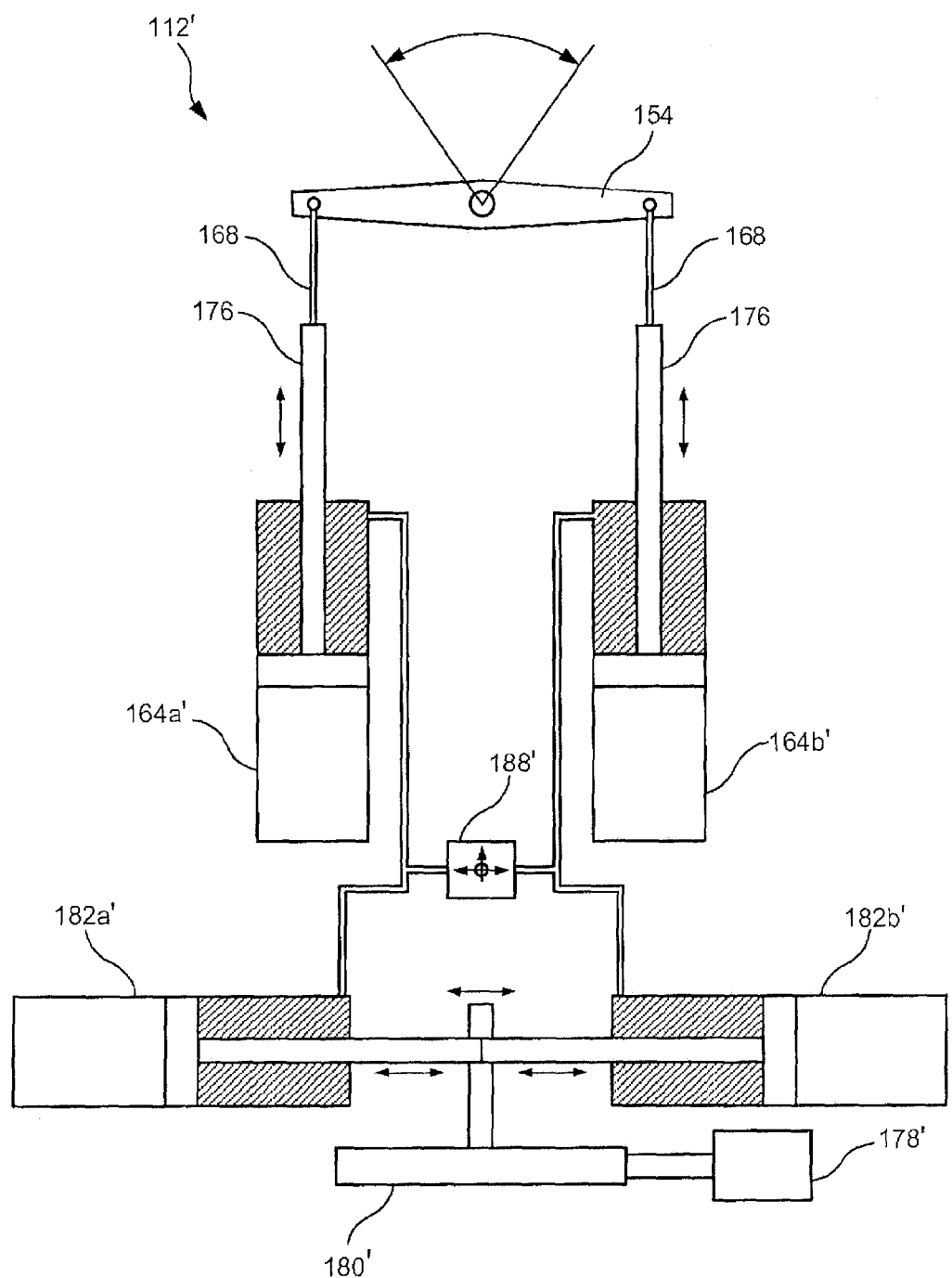
FIG. 8 shows a schematic diagram of an alternate embodiment of the hydraulic unit of FIG. 7.

As shown in FIG. 7, the hydraulic unit 112 may supply hydraulic force through the cylinders 164 to tendons 168 to angulate the plate 154 via a motor 178 and a pump 180 that draws fluid from a reservoir 182. The hydraulic unit 112 further includes a pressure relief valve 184, a selector valve 186 and a bypass valve 188. The pump 180 draws fluid from the reservoir 182, which flows to the pressure relief valve 184 as it leaves the pump 180. The pressurized fluid is then directed either back to the reservoir 182 or on to the selector valve 186. The pressurized fluid may be directed back to the reservoir 182, for example, when a predetermined maximum system pressure has been reached. The selector valve 186 may have three settings. In a first setting no fluid is permitted to pass through the selector valve 186. In a second setting, pressurized fluid passes through the selector valve 186 and into a first one of the cylinders 164a, while non-pressurized fluid from a second one of the cylinders 164b is permitted to return to the reservoir 182. In a third setting, pressurized fluid is permitted to flow through the selector valve 186 into the second cylinder 164b while non-pressurized fluid from the first cylinder 164a is permitted to return to the reservoir 182.

The hydraulic unit 112 may also be set such that the robotic device 102 may be operated in a neutral or limp mode, in which the cylinders 164 are manually movable. In the limp mode, the selector valve 186 is moved to the first setting, in which no fluid passes therethrough and the bypass valve 188 is set such that fluid passes freely therethrough. The cylinders 164 and the arms may then be manually moved to desired positions and/or orientations and then locked in the desired position. It will be understood by those of skill in the art that although the hydraulic unit 112 is shown and described with two cylinders 164a, 164b, the hydraulic unit 112 may be adapted such that any number of cylinders 164 may be used to move the plate 154.

In an alternate embodiment, a hydraulic unit 112' may supply hydraulic forces to first and second cylinders 164a', 164b' to provide angulation of the plate 154 and the arms 108, as described above in regard to the system 100. The hydraulic unit 112' may comprise a motor 178' driving a linear actuator 180' to simultaneously move first and second master cylinders 182a', 182b', respectively. Depending on a desired motion, one of the first and second master cylinders 182a', 182b' transfer pressurized fluid to one of the first cylinder 164a' and second cylinder 164b', respectively. Similarly to the hydraulic unit 112, the hydraulic unit 112' may be configured in a limp mode so that the cylinders 164, and thereby the arms 108, may be manually moved, as desired. When operating in the limp mode, a bypass valve 188' is set such that fluid is allowed to pass freely therethrough.

Figure 9:
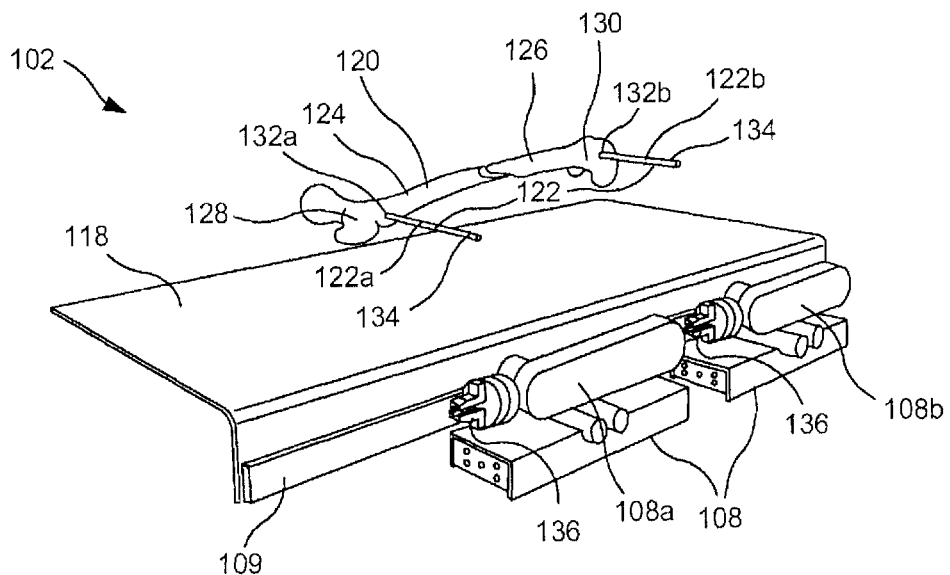
FIG. 9 shows a perspective view of the robotic device of FIG. 2 in which connectors are coupled to bone fragments.

As shown in FIG. 9, an exemplary method of use of the system 100 includes inserting one or more connectors 122 into each of a plurality of portions of the bone 120 to be repositioned relative to one another. Each of the connectors 122 may be a bone holding device such as, for example, a schanz screw, pin or clamp type device. In an exemplary embodiment, a first end 132a of a first connector 122a is inserted into a first fractured portion 124 of the bone 120 while a first end 132b of a second connector 122b is inserted into a second fractured portion 126 of the bone 120. As can be seen, in this example, the first connector 122a has been inserted into a proximal portion 128 of the bone 120 while the second connector 122b has been inserted into a distal portion 130 of the bone 120. Although in this example, two connectors 122 are shown with a single connector 122 in each of the fractured portions of the bone 120, it will be understood by those of skill in the art that any number of connectors 122 may be employed in the each of the fractured portions of the bone 120 to achieve the desired stabilization of each of the fractured portions.

Figure 10:
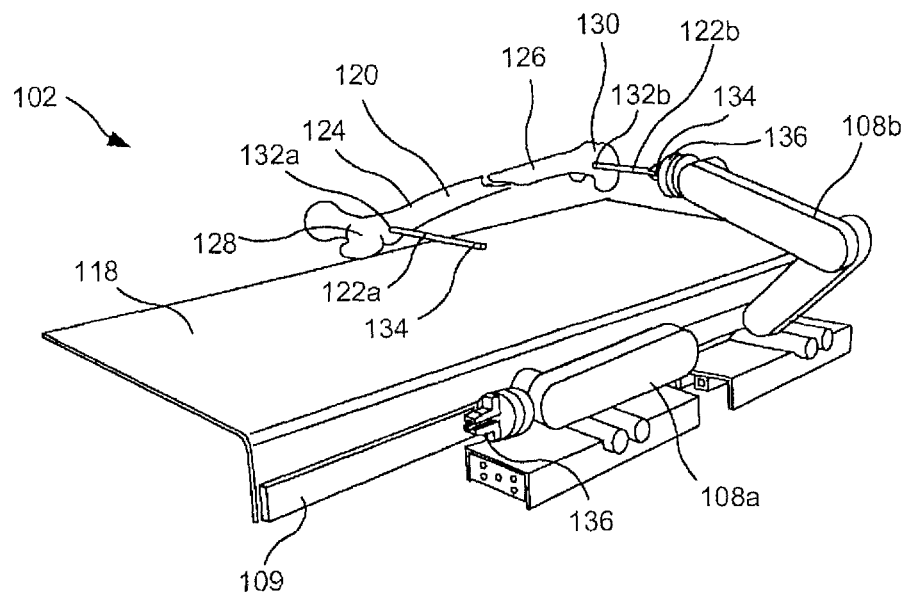
FIG. 10 shows a perspective view of the robotic device of FIG. 2, connected to a connector inserted into a fractured portion of a bone.
Figure 11:
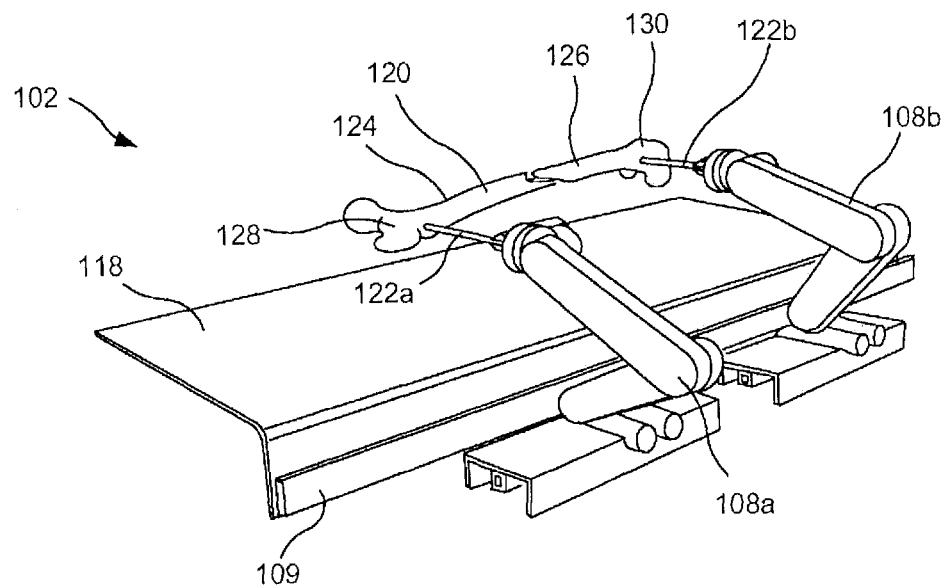
FIG. 11 shows a perspective view of the robotic device of FIG. 2, moving fractured portions of the bone to reposition the bone.

As shown in FIGS. 10-11, each of the arms 108 is connectable to the bone 120 via the connectors 120. For example, a first arm 108a is connected to the first connector 122a and a second arm 108b is connected to the second connector 122b. It will be understood by those of skill in the art, however, any number of arms 108 may be included to independently maneuver any number of fractured portions of bone relative to one another. As indicated above, each of the arms 108 may include an end effector 136 connectable to a corresponding second end 134 of a connector 122. The end effectors 136 of the arms 108 may include, for example, jaws or a grasper adapted to securely grasp the second ends 134 of the connectors 122. Alternatively, the end effectors 136 may be a protrusions or other elements configured to securely mate with the second ends 134 of the connectors 122.

To connect the end effectors 136 to the second ends 134 of the connectors 122, the robotic device 102 may be placed in the limp mode allowing each of the arms 108 to be manually moved to a position in it is connectable to a corresponding one of the connectors 122. It will be understood by those of skill in the art that the limp mode may be initiated via the user interface 106. Once the end effectors 136 have been connected to each of the connectors 122, the robotic device 102 may be switched to a locked mode in which the arms 108 are locked along all axes of movement. The encoders 116 on each of the arms 108 then supply information to the system to determine the exact position and location of each of the arms 108. This information is then used to direct movement of the arms 108 and, consequently the connectors 122 and attached portions of bone, to achieve the desired final spatial relations between the various portions of bone. Once in the locked mode, the user directs motion of the arms 108 via the user interface 106.

The user may direct motion of the arms 108 via the user interface 106 by, for example, selecting one or more of the arms and manipulating one or more joysticks or other controllers in desired directions to cause corresponding movement of the arms 108. If need be, this process may be repeated for others of the arms 108 until the desired spatial relations among the portions of bone have been achieved. As described above, the arms 108 may be moved in six linear directions and angulations via movement of the rotatable first and second portions 140, 142 and the wrist portion 152 of the arm 108. If the user interface 106 includes a personal computer, points on the fractured portions 124, 126 of the bone may be identified as vertices, which may be moved by assigning target positions to these points, as would be understood by those skilled in the art. In a preferred embodiment, the points identified as vertices may be those points on the fractured portions 124, 126 at the proximal and distal ends 128, 130, respectively, to which the arms 108 are connected. It will be understood by those of skill in the art that each of the arms 108 may be moved independently of the others to achieve the desired spatial relationship between the fragments of the bone 120. Alternatively, as will also be understood by those of skill in the art, any grouping of the arms 108 may be moved simultaneously to maintain a desired spatial relationship between any or all of the bone fragments during the movement to the desired spatial relationship. The user may continue to input instructions corresponding to a desired placement of the arms 108 and, consequently, of the bone fragments, via the user interface 106, until all of the portions of the bone 120 have been repositioned, as desired.

Figure 12:
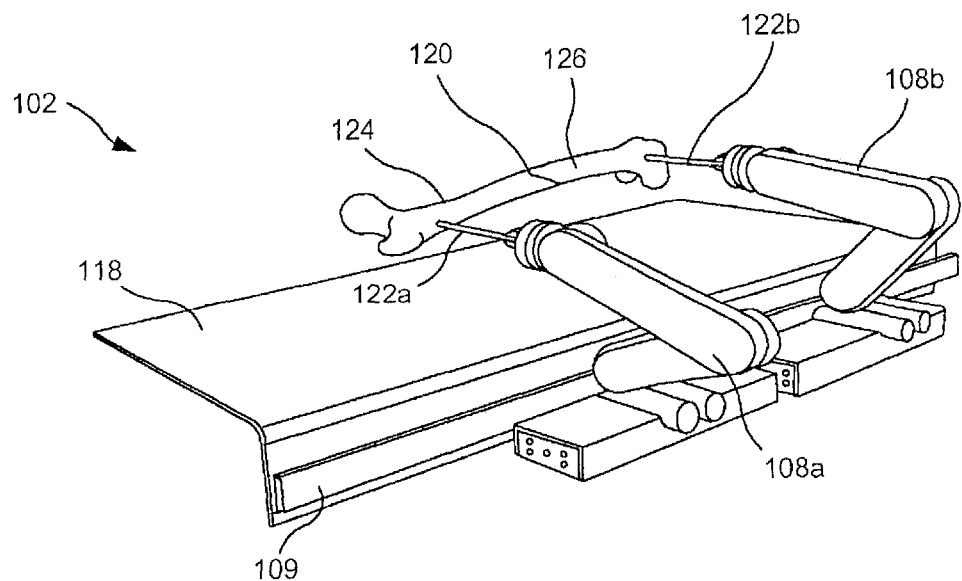
FIG. 12 shows a perspective view of the robotic device of FIG. 2, having repositioned the fractured portions of the bone.
Figure 13:
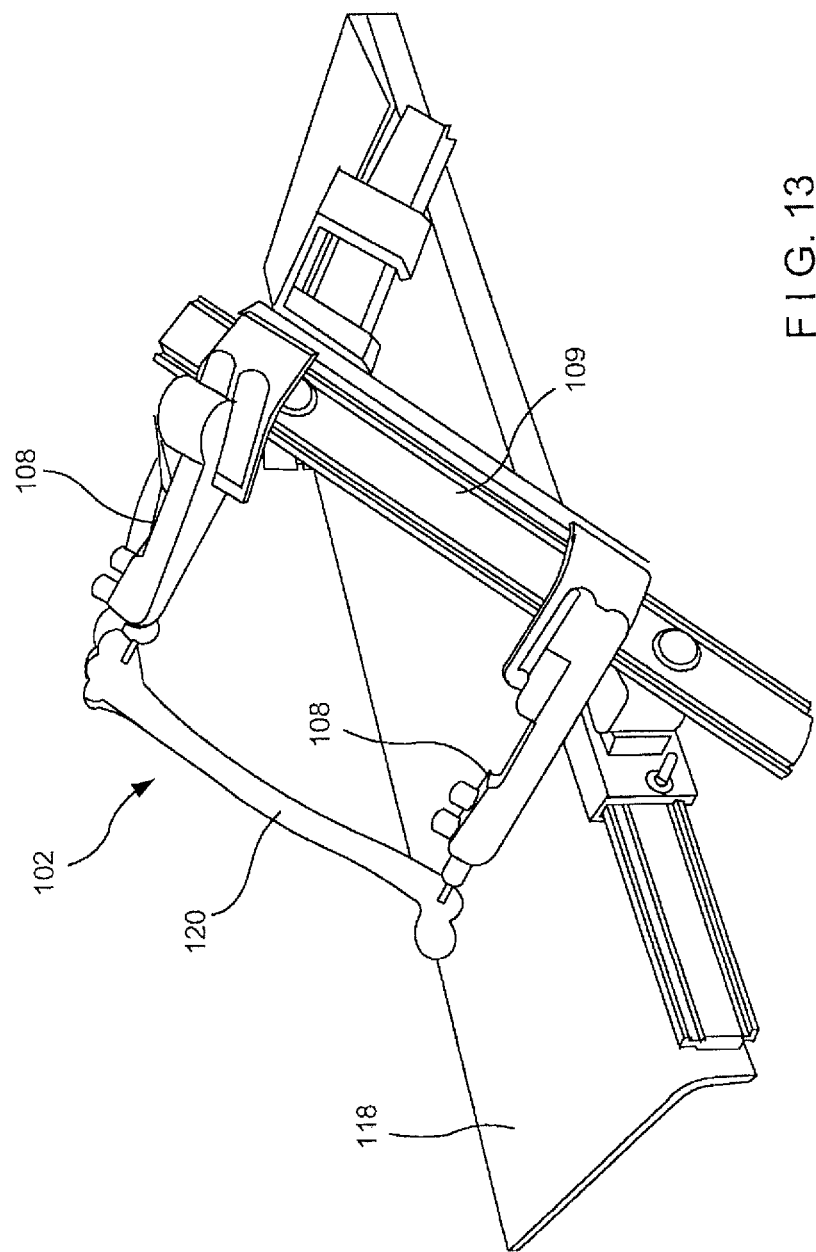
FIG. 13 shows a perspective view of the robotic device of FIG. 2, maintaining the repositioned bone fragments for fixation.

Generally, the repositioning will end when the fractured portions 124, 126 of the bone 120 have been realigned resembling as closely as possible their alignment before the fracture, as shown in FIG. 12. However, the system 100 may be used to maintain any alignment of the bone 120 desired for proper fixation. For example, as shown in FIG. 13, the robotic device 102 may rotate the bone 120 relative to the operating table 118 to a position designed to facilitate insertion of a fixation device, such as an intramedullary nail. The arms 108 may rotate the bone 120 via rotation of the longitudinal element 109, to which the arms 108 are coupled, relative to the table 118.

In an alternative embodiment, at least one of the arms 108 may be connected to a connector/connectors that holds a carriage that cradles a proximal or terminal portion of a limb of the fractured bone 120. The limb may be attached to the carriage through bone connectors or simply rested on the carriage with an appropriate bolster. The carriage facilitates a placement of the bone 120 in a desired spatial position such that the bone 120 may be reduced or positioned for the introduction of the fixation device.

It will be apparent to those skilled in the art that various modifications and variations can be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A method, comprising;
    securing a first bone fragment to a first bone fixation element and a second bone fragment to a second bone fixation element;
    coupling a distal end of a first arm to the first bone fixation element and a distal end of a second arm to the second bone fixation element, each of the first and second arms extending between the distal end and a proximal end coupled to a frame, the frame including a longitudinal element;
    receiving data corresponding to a desired final position of the first and second bone fragments relative to one another; and
    controlling a mechanical unit to a move the first and second arms relative to one another to achieve the desired final position of the bone fragments, the first and second arms moving at least longitudinally along the frame, wherein the longitudinal element of the frame is configured to rotate in order to rotate the first and second arms relative to the frame and the first and second arms are rotatable relative to a longitudinal axis of the longitudinal element of the frame.

2. The method of claim 1, wherein each of the first and second arms includes first and second portions rotatably coupled to one another.

3. The method of claim 1, wherein each of the first and second arms includes first and second portions pivotably coupled to one another.

4. The method of claim 1, further comprising determining a position of each of the bone fragments based on data received from encoders attached to each of the first and second arms.

5. The method of claim 1, further comprising visualizing the bone fragments on an imaging device to determine a desired spatial relationship of the bone fragments.

6. The method of claim 1, wherein the data corresponding to a desired final position of the first and second bone fragments relative to one another is input by a user to the controller which controls the first and second arms to achieve the desired spatial relation.

7. The method of claim 1, wherein the data corresponding to a desired final position of the first and second bone fragments relative to one another is input by a user through manipulation of controls directing the motion of the first and second bone fragments relative to one another as they are moved by the controller which controls the first and second arms move the first and second bone fragments as directed by the user to achieve the desired spatial relation.

8. The method of claim 1, further comprising positioning a limb of the first and second bone fragments via a carriage that cradles a portion of the limb, the carriage movable via a third arm couplable to the carriage.

9. A method, comprising;
    securing a first bone fragment to a first bone fixation element and a second bone fragment to a second bone fixation element;
    coupling a distal end of a first arm to the first bone fixation element and a distal end of a second arm to the second bone fixation element, each of the first and second arms extending between the distal end and a proximal end coupled to a frame, the frame including a longitudinal element, the first arm including a first wrist portion and a first coupling adapted to lockingly engage the first bone fixation element, the first wrist portion being attached to the distal end of the first arm, pivotally connecting the first coupling to the distal end of the first arm, the first wrist including a first plate pivotally attached to a proximal end of the first coupling for rotation about a first shaft extending through the first wrist;
    receiving data corresponding to a desired final position of the first and second bone fragments relative to one another; and
    controlling a mechanical unit to a move the first and second arms relative to one another to achieve the desired final position of the bone fragments, the first and second arms moving at least longitudinally along the frame, wherein the longitudinal element of the frame is configured to rotate in order to rotate the first and second arms relative to the frame.

10. The method of claim 9, wherein the second arm includes a second wrist portion and a second coupling adapted to lockingly engage the second bone fixation element, the second wrist portion being attached to the distal end of the second arm, pivotally connecting the second coupling to the distal end of the second arm.

11. The method of claim 10, wherein the second arm includes a second plate pivotally attached to a proximal end of the second coupling for rotation about a second shaft extending through the second arm.

12. The method of claim 11, wherein the mechanical unit includes a plurality of first hydraulic cylinders, each of the first hydraulic cylinders being attached to a proximal surface of the first plate to pivot the first plate about the first shaft.

13. The method of claim 12, wherein the mechanical unit includes a plurality of second hydraulic cylinders, each of the second hydraulic cylinders being attached to a proximal surface of the second plate to pivot the second plate about the second shaft.

14. The method of claim 12, wherein the first hydraulic cylinders are arranged substantially equidistant from one another about a perimeter of the first plate.

15. The method of claim 13, wherein the second hydraulic cylinders are arranged substantially equidistant from one another about a perimeter of the second plate.

* * * * *